United States Patent [19]

MacMahon

[11] Patent Number: 5,388,143
[45] Date of Patent: Feb. 7, 1995

[54] ALIGNMENT METHOD FOR RADIOGRAPHY AND RADIOGRAPHY APPARATUS INCORPORATING SAME

[75] Inventor: Heber MacMahon, Chicago, Ill.

[73] Assignee: Arch Development Corporation, Chicago, Ill.

[21] Appl. No.: 158,599

[22] Filed: Nov. 26, 1993

[51] Int. Cl.⁶ .................................................. A61B 6/08
[52] U.S. Cl. ....................................... 378/206; 378/154
[58] Field of Search ................ 378/206, 205, 154, 155

[56] References Cited

U.S. PATENT DOCUMENTS

| | | |
|---|---|---|
| 2,111,903 | 3/1938 | Rona . |
| 2,355,066 | 8/1944 | Goldfield et al. . |
| 3,304,427 | 2/1967 | Peyser . |
| 3,705,984 | 12/1972 | Westenberger . |
| 3,979,595 | 9/1976 | Merchant . |
| 4,092,544 | 5/1978 | Grim . |
| 4,246,486 | 1/1981 | Madsen . |
| 4,380,087 | 4/1983 | Tanaka . |
| 4,455,672 | 6/1984 | Hahn et al. . |
| 4,563,586 | 1/1986 | Jordan . |
| 4,752,948 | 6/1988 | MacMahon . |
| 5,241,578 | 8/1993 | MacMahon . |
| 5,283,808 | 2/1994 | Cramer et al. ................ 378/206 |

OTHER PUBLICATIONS

Heather Carswell, "Portable chest films make poor showing against CT," *Imaging News*, pp. 11–14 (May 1991).

Advertisement titled "Precision Plus," by Gammex Lasers (1989).

Primary Examiner—Craig E. Church
Attorney, Agent, or Firm—Arnold, White & Durkee

[57] ABSTRACT

An alignment method and system for aligning an anti-scatter grid with an x-ray source of a radiographic apparatus, to facilitate accurate alignment of the central x-ray beam of the x-ray source of the radiographic apparatus with a focused grid. The present invention uses a first light projector that is substantially fixed relative to the x-ray source, which produces a first alignment image that is substantially fixed relative to the grid. Also included is a second light projector that is substantially fixed relative to the grid, and that produces a second alignment image that is substantially fixed relative to the x-ray source. The first light projector is preferably the collimator light included within the collimator housing of the x-ray apparatus, and the second light projector is preferably a laser light source, that is attachable to a grid cassette holding the grid.

18 Claims, 4 Drawing Sheets

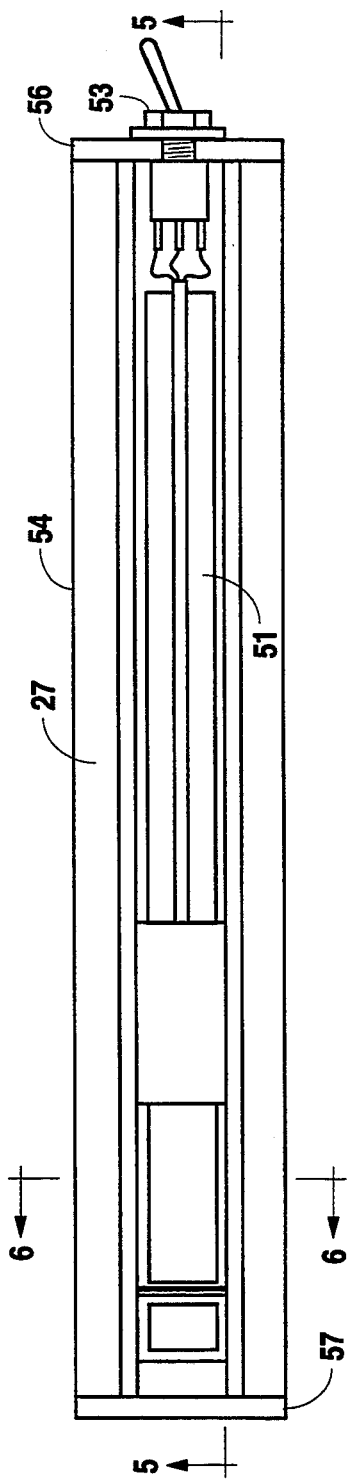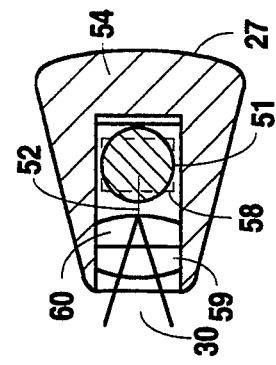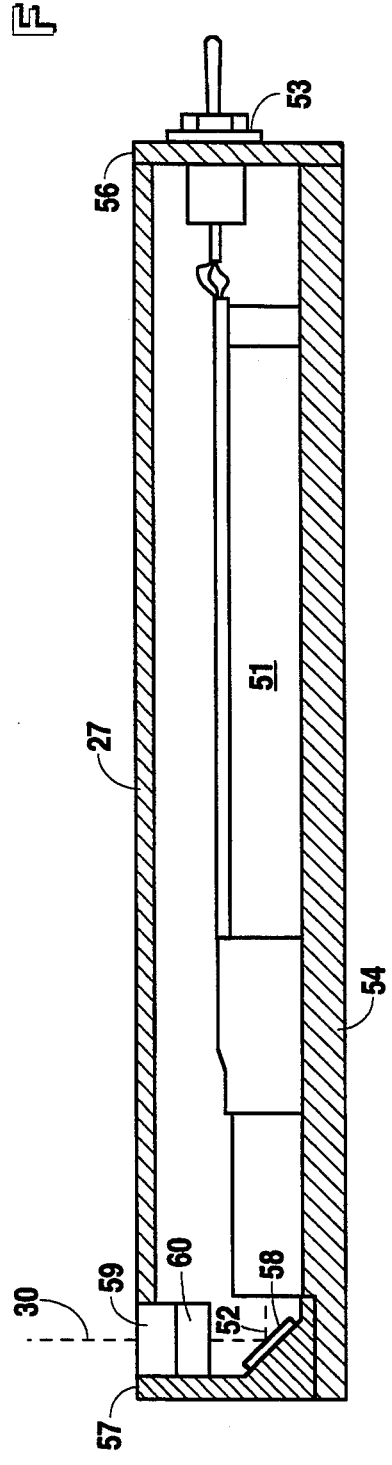

ALIGNMENT METHOD FOR RADIOGRAPHY AND RADIOGRAPHY APPARATUS INCORPORATING SAME

BACKGROUND OF THE INVENTION

The present invention relates to an optical alignment system for radiography.

Although the clinical importance of portable x-ray examinations is beyond question, the image quality may be inferior to that obtained with fixed radiograph apparatus in an x-ray department. This inferior image quality is commonly attributed to intrinsic limitations of portable radiography apparatus, however, it is in fact due mainly to uncontrolled scattered radiation which fogs the radiograph, thus reducing contrast and obfuscating diagnostic information.

Use of an accurately aligned anti-scatter grid can provide consistently high image quality, but precise alignment of the grid relative to the x-ray source is important for good results.

For portable radiography, good results can be achieved with a 6:1 or 8:1 anti-scatter grid, provided that the x-ray beam energy is no greater than 90 KV, and provided that the anti-scatter grid is accurately aligned with respect to the x-ray source. Referring to FIG. 1, accurate alignment of a radiographic machine 20 relative to anti-scatter grid 21 and x-ray image medium 22 is illustrated in position A while inaccurate alignment is illustrated in position B.

In the case of a conventional lead strip linear anti-scatter grid, alignment is critical only in the dimension across the grid lines. Moderate angulation error along the direction of the grid lines does not significantly impair image quality. In other words, referring again to FIG. 1, moderate misalignment about a horizontal axis lying within the plane of the page is not so critical, whereas alignment about an axis perpendicular to the plane of the page is important.

Further, with a focused anti-scatter grid, it is also desirable for central x-ray beam 23 of x-ray machine 20 to be centered accurately with respect to anti-scatter grid 21. Further, variations in focus distance when using a focused grid are important, but mainly affect film density provided that the x-ray machine 20 is properly centered and aligned relative to anti-scatter grid 21. In the case of a two dimensional grid, for example a cross-hatched grid or pinhole grid, alignment is also important in two dimensions.

An approach that addresses this alignment problem is presented in U.S. Pat. No. 4,752,948 issued Jun. 21, 1988, and assigned to the same assignee as the present application. The disclosure of this patent is expressly incorporated herein by reference. While adequately addressing the problem of alignment between the x-ray beam and anti-scatter grid in a portable x-ray apparatus, this patented device presents a mechanical system which has proven somewhat difficult to retrofit to existing portable x-ray apparatus, or to use with very ill patients who are unable to cooperate.

Another system that addresses this alignment problem is presented in U.S. Pat. No. 5,241,578, issued Aug. 31, 1993, and assigned to the same assignee as the present application. The disclosure of this patent is also expressly incorporated herein by reference. This device employs a laser device mounted to the collimator housing of a portable x-ray machine with a mirror reflector on the grid cassette, thus eliminating any mechanical connection between the x-ray machine and the grid cassette. However, modification of the x-ray unit to incorporate the laser device is required, which, once again, renders the device somewhat difficult to retrofit to existing portable x-ray machines.

SUMMARY OF THE INVENTION

The present invention in large part solves the above-noted problems in prior approaches to alignment between an x-ray apparatus and an anti-scatter grid by providing a simple grid alignment system which may easily be retrofitted to existing x-ray equipment.

To facilitate accurate alignment and centering of the central x-ray beam with a focused grid in a clinical setting, the present invention employs a light projector, for example, a laser light projector, mounted in or on the grid cassette. The image produced by the light projector is used in combination with the image produced by the collimation light within the collimator housing, to align and center the grid cassette relative to the collimator housing, and to place the grid cassette at the proper distance from the collimator housing.

The light projector is positioned to project a light beam from the grid cassette toward the collimator housing where the light beam impinges upon an indicating surface which is substantially fixed relative to the collimator housing. The image produced by the light beam on the indicating surface in combination with the image produced by the collimation light on the surface of the grid cassette facilitates centering the grid cassette with respect to the central x-ray beam of the x-ray source, ensures that the grid and x-ray image medium are aligned substantially perpendicular to the central x-ray beam of the x-ray source, and facilitates placement of the grid cassette at the proper focal distance from the x-ray source.

BRIEF DESCRIPTION OF THE DRAWINGS

FIGS. 4, 5 and 6 are an embodiment of a light projector in accordance with the present invention.

DETAILED DESCRIPTION

Figure 1:
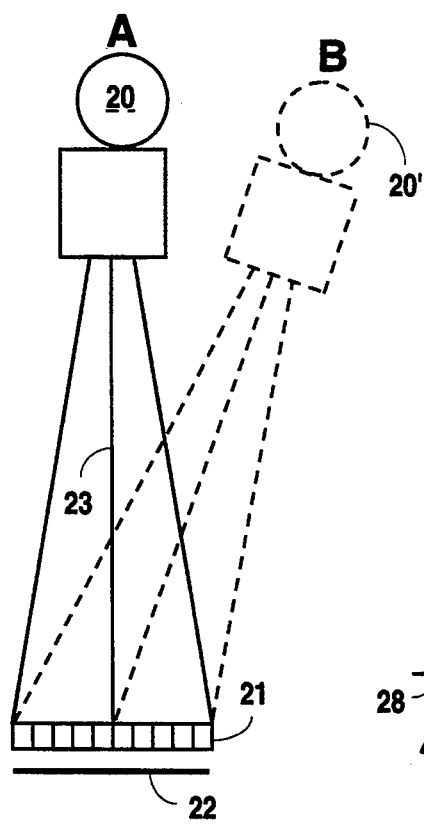
FIG. 1 is a schematic representation of misalignment between a radiography machine and a grid cassette.
Figure 2:
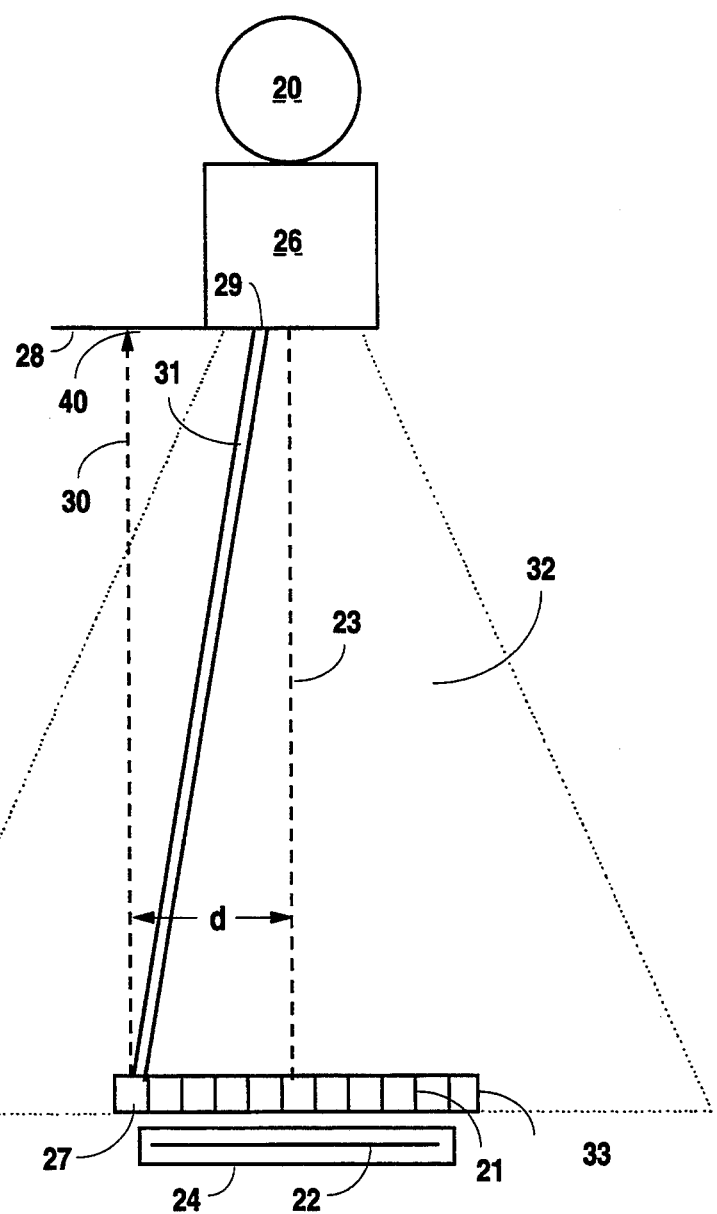
FIG. 2 is a schematic representation of a x-ray apparatus incorporating the optical alignment system of the present invention.

Referring to FIG. 2, presented is a block diagram of a x-ray apparatus incorporating the optical alignment system of the present invention. The system includes x-ray machine 20 and grid cassette 33 including anti-scatter grid 21, which is located between x-ray machine 20 and x-ray image medium cassette 24. X-ray image medium cassette 24 holds x-ray image medium 22. X-ray image medium 22 may be, for example, x-ray sensitive film, photostimuable phosphor plate or area-type digital receptor. Other types of x-ray sensitive imaging media may also be acceptable without departing from the scope of the invention. Attached to or incorporated within grid cassette 33 is light projector 27 which projects light beam 30 from grid cassette 33 toward collimator housing 26. An alignment image 40 of light beam 30 is formed upon indicating surface 28 which is substantially fixed relative to collimator housing 26.

In addition, an opaque line 29 (shown in more detail with reference to FIG. 9) is applied to the transparent front surface of collimator housing 26, and casts a second alignment image, in the form of shadow 31, on the surface of grid cassette 33 within the collimation field 32 projected by the collimation light within collimation housing 26.

As explained in more detail below, the alignment image 40 produced by light projector 27, in combination with the alignment image 31 within collimation field 32 projected by the collimation light within collimation housing 26, ensures proper angulation alignment of grid cassette 33 relative to the x-ray source within x-ray machine 20. Further, when shadow 31 is coincident with a predetermined portion of grid cassette 33 (for example the edge of grid cassette 33), grid cassette 33 is located at the proper focal distance from the x-ray source within x-ray machine 20. Further, adjustment of grid cassette 33 so that the light beam 30 forms alignment image 40 on indicating surface 28 at a predetermined location (for example a predetermined distance from central x-ray beam 23) ensures centering of the x-ray machine 20 with respect to grid cassette 33.

Figure 3:
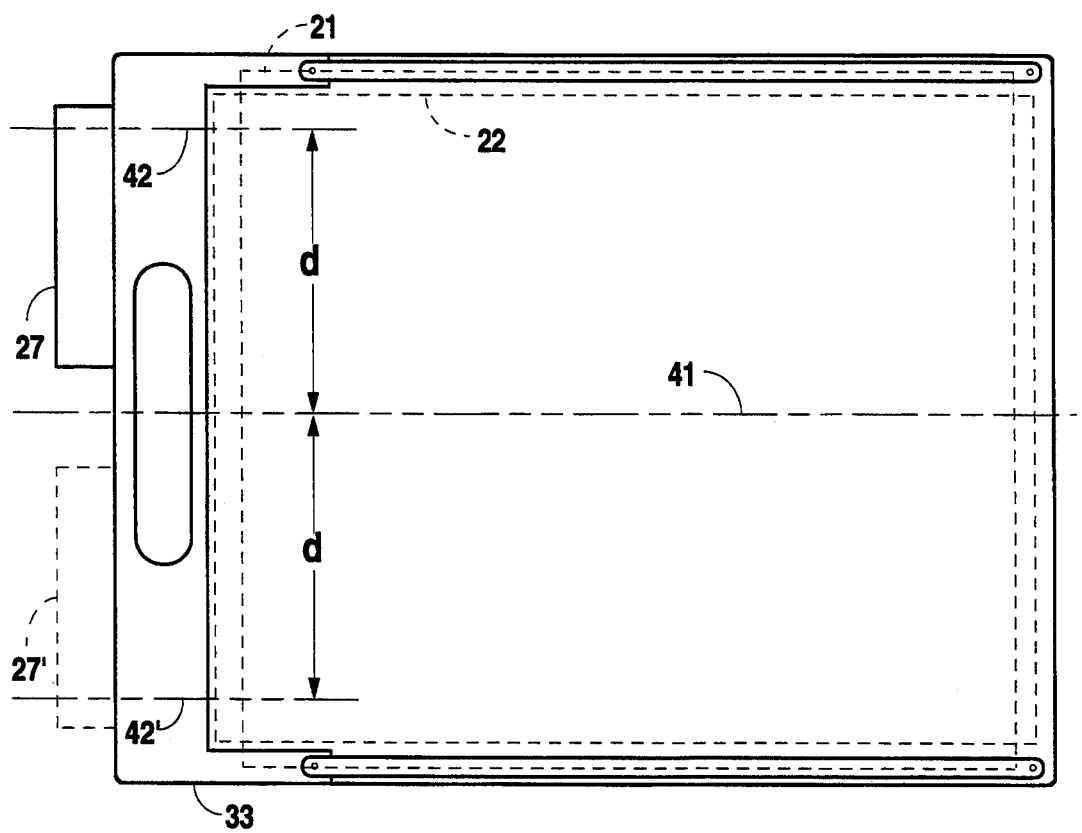
FIG. 3 is an embodiment of a grid cassette incorporating the present invention.

Referring now to FIG. 3, disclosed is an embodiment of grid cassette 33 incorporating a light beam projector 27 in accordance with the present invention. In operation, x-rays from x-ray machine 20 impinge upon grid cassette 33 from the back side of FIG. 3. Within grid cassette 33 is included anti-scatter grid 21 which, in this embodiment, is a 6:1 focused linear grid. As mentioned above, when using a linear grid, alignment is critical across the grid lines, and is less critical along the direction of the grid lines. The grid lines of grid 21 within grid cassette 33 run substantially parallel to central line 41, which, in turn, is substantially parallel to the longitudinal direction of the lead slats in anti-scatter grid 21 contained within grid cassette 33. Held by grid cassette 33 is x-ray image medium 22.

Formed with, or attachable to, grid cassette 33 is light projector 27 which, as described in more detail below, projects a light beam toward the collimator housing (i.e., into the paper as shown in FIG. 3), the light beam being substantially coplaner with line 42, and being approximately at a distance, d, from center line 41 of grid cassette 33. In accordance with the present invention the distance, d, is substantially equal to the distance between the target 61 appearing on indicating surface 28 (see also FIG. 8), and the central x-ray beam 23 of x-ray machine 20. In one embodiment of the present invention, distance, d, is approximately equal to 8 inches (20.3 cm). Light projector 27 may also be placed in the position 27' to project a light beam toward x-ray machine 20 which is substantially coplaner with line 42' shown in FIG. 3.

Referring now to FIGS. 4, 5 and 6, shown are the details of an illustrative embodiment of light projector 27, in accordance with the present invention. FIG. 4 is a plan view of light projector 27, FIG. 5 is a sectional view of light projector 27 taken through Section 5—5 of FIG. 4, and FIG. 6 is a sectional view of light projector 27 taken through Section 6—6 of FIG. 4.

In one embodiment of the invention, light projector 27 includes laser light beam projector 51 which projects a laser light beam 52 which is substantially circular or elliptical in cross-section. Laser light beam projector 51 may be, for example, a 4 mW laser pointer available from Lyte Optronics; however, other types of light sources (laser or otherwise) may also be acceptable.

Laser light beam projector 51 is turned on and off by electrical switch 53. Laser light beam projector 51 is contained within housing 54 which is substantially wedge-shaped in cross section as shown in FIG. 6. This wedge-shape permits light projector 27 to be angled slightly toward the middle of grid cassette 33, which ensures that the light beam 30 produced by light beam projector 27 will intersect imaging surface 28 which is attached to collimator housing 26 (see also FIGS. 2 and 8). This angulation is shown more clearly with reference to FIG. 7.

Housing 54 of light projector 27 is closed by endcaps 56 and 57, endcap 56 holding electrical switch 53, and endcap 57 supporting mirror 58 and cylinder lenses 59 and 60.

Cylinder lenses 59 and 60 function to convert laser beam 52 into a substantially fan-shaped light beam 30. In one embodiment of the present invention, fan-shaped light beam 30 has a width of approximately 6 inches (15.2 cm) at a distance of 40 inches (102 cm) from light projector 27.

Figure 7:
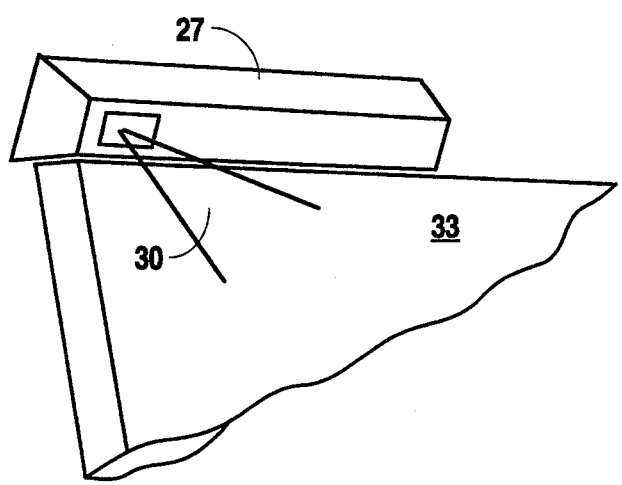
FIG. 7 illustrates the attachment of the light projector of FIG. 4 to a grid cassette, in accordance with the present invention.

Referring now to FIG. 7, shown is an isometric view of light projector 27 affixed to grid cassette 33. Light projector 27 may be attached to grid cassette 33 by any convenient means, for example, magnets, mechanical clamps, screws, or the like. Although light projector 27 is preferably removable from grid cassette 33, light projector 27 may also be integrally formed with grid cassette 33, without departing from the spirit or scope of the present invention.

Figure 8:
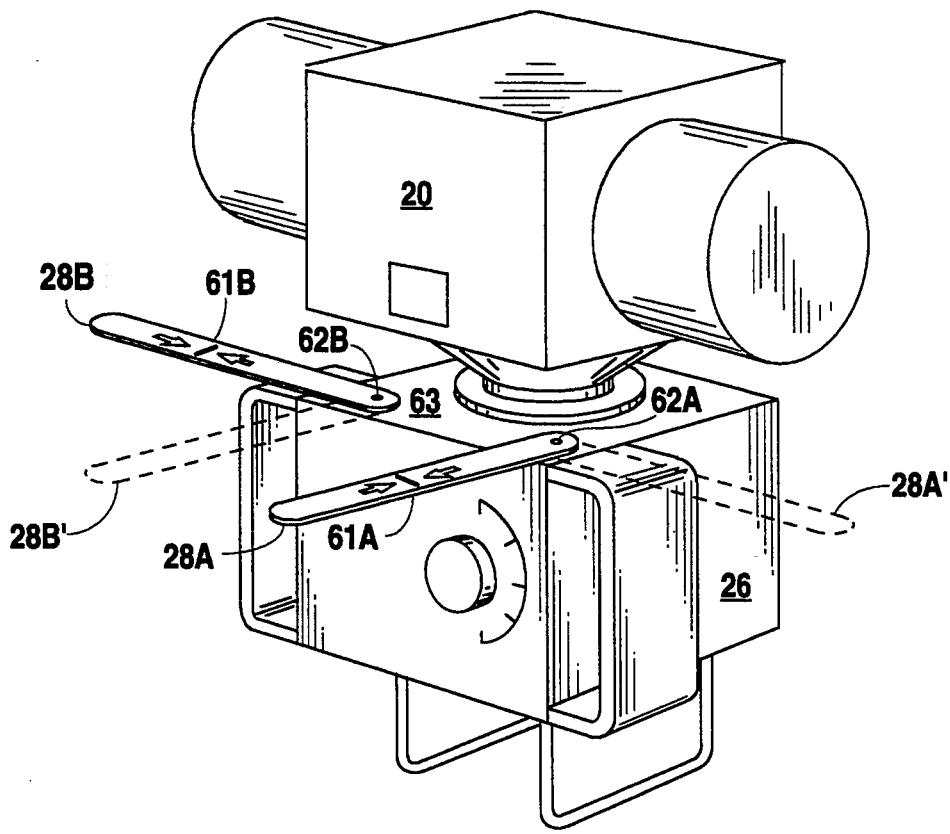
FIG. 8 illustrates the mounting of an indicating surface to the collimator housing of an x-ray apparatus, in accordance with the present invention.

Turning now to FIG. 8, presented in more detail is an exemplary configuration of x-ray machine 20 collimator housing 26 and indicating surface 28 in accordance with the present invention. In FIG. 8, indicating surfaces 28A and 28B may be mounted as shown to collimator housing 26 of a conventional, portable x-ray machine, for example, an AMX 4, portable x-ray machine available from the General Electric Company. The present invention, of course, may be used with other types of x-ray machines (portable or otherwise), and indicating surfaces 28A and 28B may in fact not be fixed to collimator housing 26, but rather may be held in place by an operator during the alignment procedure. In fact, indicating surfaces 28A and 28B may even be the hand of an operator held substantially flat and adjacent to collimator housing 26 in order to form an indicating surface. Moreover, only one indicating surface 28A or 28B may be used without departing from the scope of the invention. Indicating surfaces 28A and 28B may be of translucent plastic; however, any material upon which alignment image 40 may be formed would also be acceptable.

As described above with reference to FIG. 2, light projector 27 projects light beam 30 toward indicating surface 28 to form an alignment image 40 upon indicating surface 28. Indicating surfaces 28A and 28B may bear a mark, such as a target 61A and 61B, at a distance, d, from the central x-ray beam. 23 of x-ray machine 20. As shown in FIG. 8, indicating surfaces 28A and 28B may be mounted to collimator housing 26 through use of pivot pins 62A and 62B, or the like, to permit indicating surfaces 28A and 28B to be pivoted to positions 28A' and 28B' to permit alignment of a grid extending in either of two transverse directions. Indicating surfaces 28A and 28B may also be pivoted to storage positions adjacent surface 63 of collimator housing 26.

Figure 9:
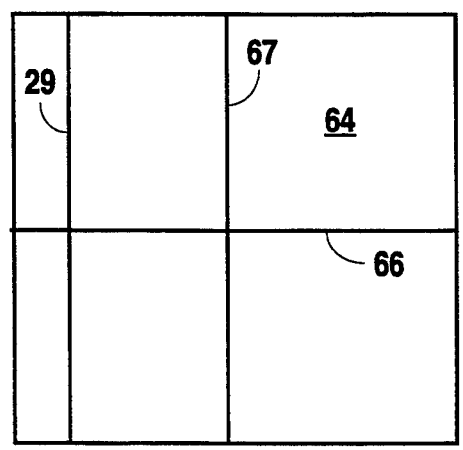
FIG. 9 is the transparent collimator front surface of a radiographic apparatus in accordance with the present invention.

Referring now to FIG. 9, presented is the transparent cover plate 64 of collimator housing 26 in accordance with the present invention. Cover plate 64 includes standard cross-hairs 66, 67, the shadows of which are projected on a patient during the alignment of x-ray machine 20 (see also FIG. 2). The intersection of cross-hairs 67 and 68 is substantially coincident with central x-ray beam 23. Added to transparent cover plate 64 is an opaque focus line 29, which as described above with reference to FIG. 2, casts an alignment image in the form of a shadow onto the surface of grid cassette 33 holding anti-scatter grid 21.

During alignment of x-ray machine 20 in accordance with the present invention, a technician may position x-ray machine 20 at a distance from grid cassette 23 until a first alignment image (in the form of shadow 31 of opaque line 29) appearing on the surface of grid 33 coincides with a predetermined portion of grid cassette 33, for example, the edge of grid cassette 33. Then, while maintaining shadow 31 upon the predetermined portion of grid cassette 33, the operator may adjust the angulation of grid cassette 33 until the second alignment image (alignment image 40) produced by light beam 30 upon indicating surface 28A or 28B is at or near the desired position (target 61A or 61B) on indicating surface 28A or 28B. While coincidence between the alignment image 40 produced on imaging surface 28A (or 28B) and the target 61A (or 61B) formed on indicating surface 28A (or 28B) is desirable, it has been determined that when alignment image 40 falls within approximately 3 inches (7.6 cm) of target 61A (or 61B), x-ray image degradation due to grid misalignment will be minimal. For example, with a 48 inch (122 cm) focus distance of a focused grid, a 1 inch (2.5 cm) displacement of alignment image 40 from the target 61A (or 61B) on indicating surface 28A (or 28B) corresponds to approximately 1° of angulation error.

Although the present invention has been developed primarily for bedside chest radiography, the system is applicable to all x-ray examination.

What is claimed is:

1. A method of aligning an x-ray source and an anti-scatter grid in a radiography apparatus, comprising:
   transmitting a first alignment image from a first position substantially fixed relative to said x-ray source;
   transmitting a second alignment image from a second position substantially fixed relative to said anti-scatter grid; and
   adjusting a relative position between said x-ray source and said anti-scatter grid to place said first alignment image substantially at a first predetermined position relative to said anti-scatter grid while placing said second alignment image substantially at a second predetermined position relative to said x-ray source.

2. The method of claim 1, said step of transmitting said second alignment image comprising, transmitting laser light from said second position.

3. The method of claim 2, said step of transmitting laser light, comprising transmitting a fan beam of laser light from said second position.

4. The method of claim 1, further comprising, forming said first alignment image upon an indicating surface substantially fixed relative to said grid.

5. The method of claim 4, said imaging surface being a surface of a grid cassette containing said grid.

6. The method of claim 1, further comprising, forming said second alignment image upon an indicating surface substantially fixed relative to said x-ray source.

7. The method of claim 6, said second predetermined position comprising a target formed on said indicating surface.

8. A method of aligning an x-ray source and an anti-scatter grid in a radiography apparatus, comprising:
   projecting light from a first position substantially fixed relative to said grid;
   forming an image of said light projected from said first position at a second position substantially fixed to said x-ray source;
   projecting light from a third position substantially fixed relative to said x-ray source; and
   forming an image of said light projected from said third position at a fourth position substantially fixed relative to said grid.

9. The method of claim 8, said step of projecting light from said first position, comprising, projecting a fan beam of light from said first position, a plane of said fan beam being substantially parallel to grid lines within said anti-scatter grid.

10. A grid alignment system for use in radiographic apparatus, comprising:
    an anti-scatter grid, positionable between an x-ray imaging medium and an x-ray source;
    a first light projector, substantially fixed relative to said x-ray source, for producing a first alignment image on a first indicating surface, said first indicating surface being substantially fixed relative to said grid; and
    a second light projector substantially fixed relative to said grid for producing a second alignment image on a second indicating surface, said second indicating surface being substantially fixed relative to said x-ray source, said first and second alignment images together providing an indication of alignment between said grid and said x-ray source.

11. The system of claim 10, said second light projector being integrally formed with a grid cassette holding said grid.

12. The system of claim 10, said second light projector being removably attached to a grid cassette holding said grid.

13. The system of claim 10, said second light projector being a laser light projector.

14. The system of claim 10, said first light projector being a collimator light.

15. The system of claim 10, said second alignment image being a line substantially parallel to grid lines within said grid.

16. The system of claim 10, said first indicating surface comprising a surface of a grid cassette holding said grid.

17. The system of claim 10, said second indicating surface being attached to a collimator housing of said radiographic apparatus.

18. A portable x-ray apparatus which is sufficiently mobile to be brought to bedside for making radiographs of a patient, comprising:

an x-ray source adjustable in orientation to allow the exposure of radiographs of portions of a patient in a plurality of orientations at bedside;

an anti-scatter grid positionable between said x-ray source and a x-ray imaging medium;

a first light beam projector substantially fixed relative to said grid, for projecting a first alignment image upon a first indicating surface, said first indicating surface being substantially fixed relative to said x-ray source; and a second light beam projector, substantially fixed relative to said x-ray source, for projecting a second alignment image upon a second indicating surface, said second indicating surface being substantially fixed relative to said x-ray source.

* * * * *